US00PP23715P2

(12) United States Plant Patent
Scott

(10) Patent No.: US PP23,715 P2
(45) Date of Patent: Jul. 2, 2013

(54) ***CORDYLINE* PLANT NAMED 'ALBATROSS'**

(50) Latin Name: *Cordyline baueri*
Varietal Denomination: Albatross

(76) Inventor: Gordon Scott, Whenuapai (NZ)

( * ) Notice: Subject to any disclaimer, the term of this patent is extended or adjusted under 35 U.S.C. 154(b) by 114 days.

(21) Appl. No.: 13/066,016

(22) Filed: Apr. 5, 2011

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — June Hwu
(74) *Attorney, Agent, or Firm* — Mark P. Bourgeois

(57) ABSTRACT

A new cultivar of *Cordyline* plant named 'Albatross' that is characterized by dark purple leaves and a large overall size.

2 Drawing Sheets

Botanical classification: *Cordyline baueri.*
Variety Denomination: 'Albatross'.

BACKGROUND OF THE INVENTION

The present invention relates to a new and distinct cultivar of *Cordyline baueri* and hereinafter referred to by the cultivar name 'Albatross'. The new cultivar originated from seed collected from the open pollination of the female or seed parent plant *Cordyline baueri* 'Falcon'. The exact male parent plant is unknown. The resulting seeds were subsequently grown in a seed bed in a cultivated area of Whenuapai, New Zealand. 'Albatross' was selected as a single plant within the progeny by the inventor in 1999.

The new cultivar was first asexually propagated by tissue culture in Hastings, New Zealand in 2005. Since that time, under careful observation, the unique characteristics of the new cultivar have been uniform, stable and reproduced true to type in successive generations of asexual reproduction.

SUMMARY OF THE INVENTION

The new *Cordyline* 'Albatross' is distinguished from other known varieties of *Cordyline*, by the following characteristics:

1. Large overall size.
2. Dark purple leaves.

The closest comparison cultivar is the female parent plant *Cordyline* 'Falcon' (U.S. Plant Pat. No. 18,931). 'Albatross' is distinguishable from 'Falcon' in having dark purple foliage and a larger overall size. 'Falcon' has brown foliage.

BRIEF DESCRIPTION OF THE DRAWINGS

The accompanying color photograph illustrates the distinguishing characteristics of the new cultivar 'Albatross'.

The photograph on sheet 1 shows an overall view of a 2 year old plant.

The photograph on sheet 2 shows an enlarged view of the flowers.

All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Cordyline* cultivar named 'Albatross'. Data was collected in Whenuapai, New Zealand from 2 year old plants. The plants were grown outdoors under natural conditions. The time of year was Summer (Southern Hemisphere). Phenotypic differences may be observed with variations in environmental, climatic, and cultural conditions, without however, any difference in genotype. Color determinations are in accordance with The 2001 Royal Horticultural Society Colour Chart except where general color terms of ordinary dictionary significance are used. The growing requirements are similar to the species and no disease problems have been observed.

Botanical classification: *Cordyline baueri* 'Albatross'.
Common name: Cabbage Tree.
Parentage: 'Albatross' originated from seed collected from open pollinated plants of the female or seed parent *Cordyline baueri* 'Falcon'. The exact male parent plant is unknown.
Type: Ornamental perennial.
Growth rate: 10 cm. per month.
Habit: Upright, clump forming.
Height: 80 cm. in height.
Spread: 90 cm. in width.
Hardiness: USDA zone 6 to zone 10.
Propagation method: Tissue Culture.
Vigor: Moderate.
Root system: Fine and fibrous.
Pinching: No.
Stem:
- *Number of stems.*—1.
- *Shape.*—Round.
- *Surface.*—Smooth.
- *Color.*—183B.
- *Size.*—Average 3 cm. in diameter and 50 cm. in length.
- *Internode length.*—1 mm.
- *Strength.*—Strong.

Foliage:
- *Leaf dimensions.*—Average 55 cm. in length and 7 cm. in width.

*Leaf shape*.—Linear.
*Leaf division*.—Simple.
*Leaf apex*.—Acute.
*Leaf base*.—Attenuate.
*Leaf margins*.—Entire.
*Color of mature leaves* (*upper and lower surfaces*).—N77A.
*Color of young leaves* (*upper and lower surfaces*).—N77A.
*Vein color* (*upper and lower surfaces*).—N77A.
*Leaf texture*.—Upper and lower surfaces: Smooth.
*Petiole color*.—200B.
*Petiole dimensions*.—1 cm. in length and 5 mm. in diameter.

Flowers:
*Inflorescence arrangement*.—Terminal panicles.
*Inflorescence size*.—31 cm. in length and 22 cm. in width.
*Quantity of flowers*.—Approximately 800.
*Flowering season*.—Spring to summer.
*Flower bud dimensions*.—5 mm. in length and 3 mm. in diameter.
*Flower bud shape*.—Ovate.
*Flower bud color*.—198C.
*Flower shape*.—Star shaped.
*Flower size*.—3 cm. in diameter.
*Number of petals*.—6.
*Petal color*.—158D.
*Fragrance*.—Moderate sweet.

Reproductive organs:
*Stamen number*.—Average 4.
*Anther dimensions*.—0.3 mm in length, 0.1 mm. in diameter.
*Anther color*.—5D.
*Number of pistils*.—1.
*Pistil length*.—2 mm.
*Stigma color*.—157D.

Fruit and seed production: Has not been observed.
Disease and pest resistance: Has not been observed.

It is claimed:

1. A new and distinct variety of *Cordyline* plant named 'Albatross' as described and illustrated.

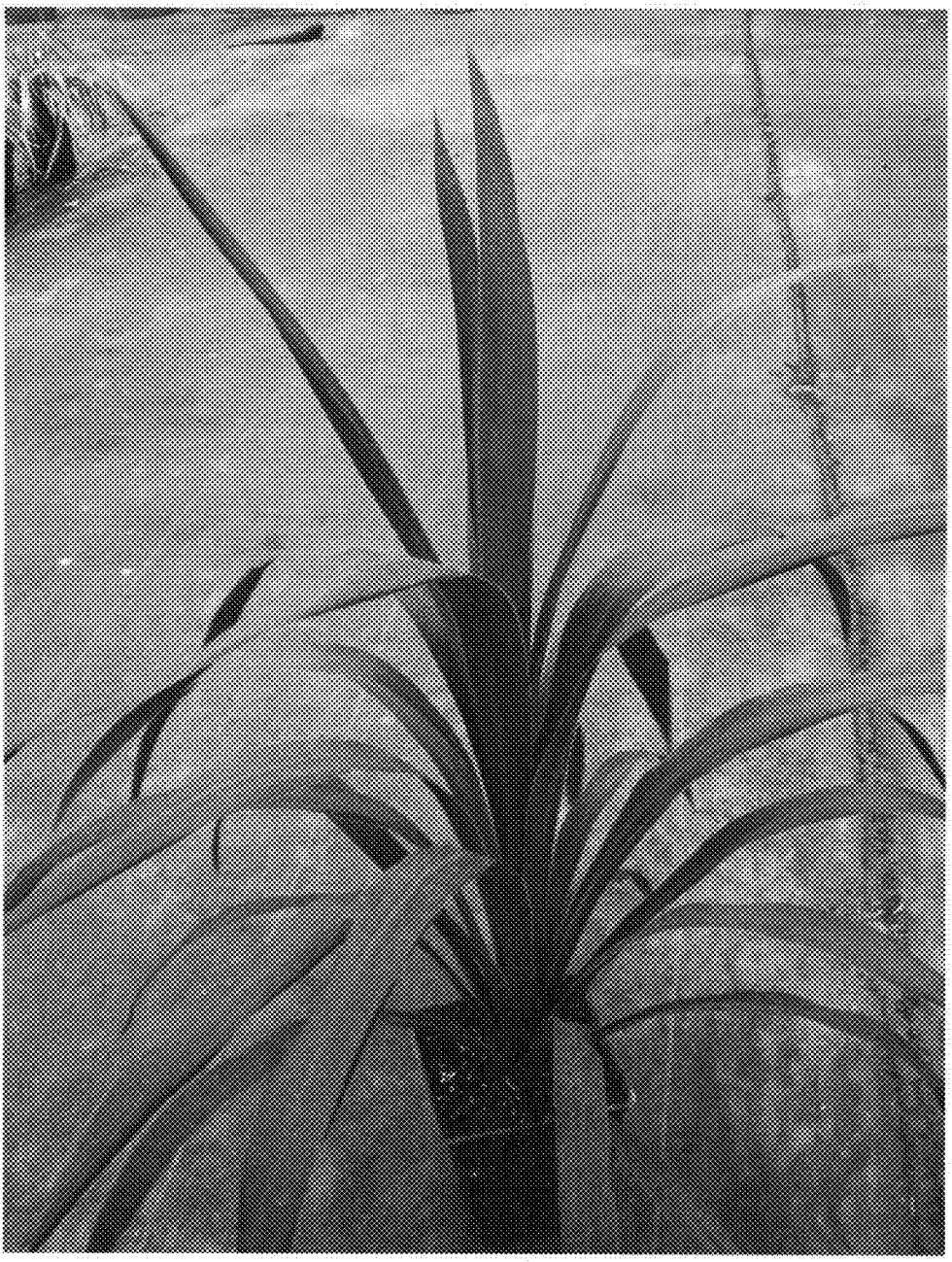

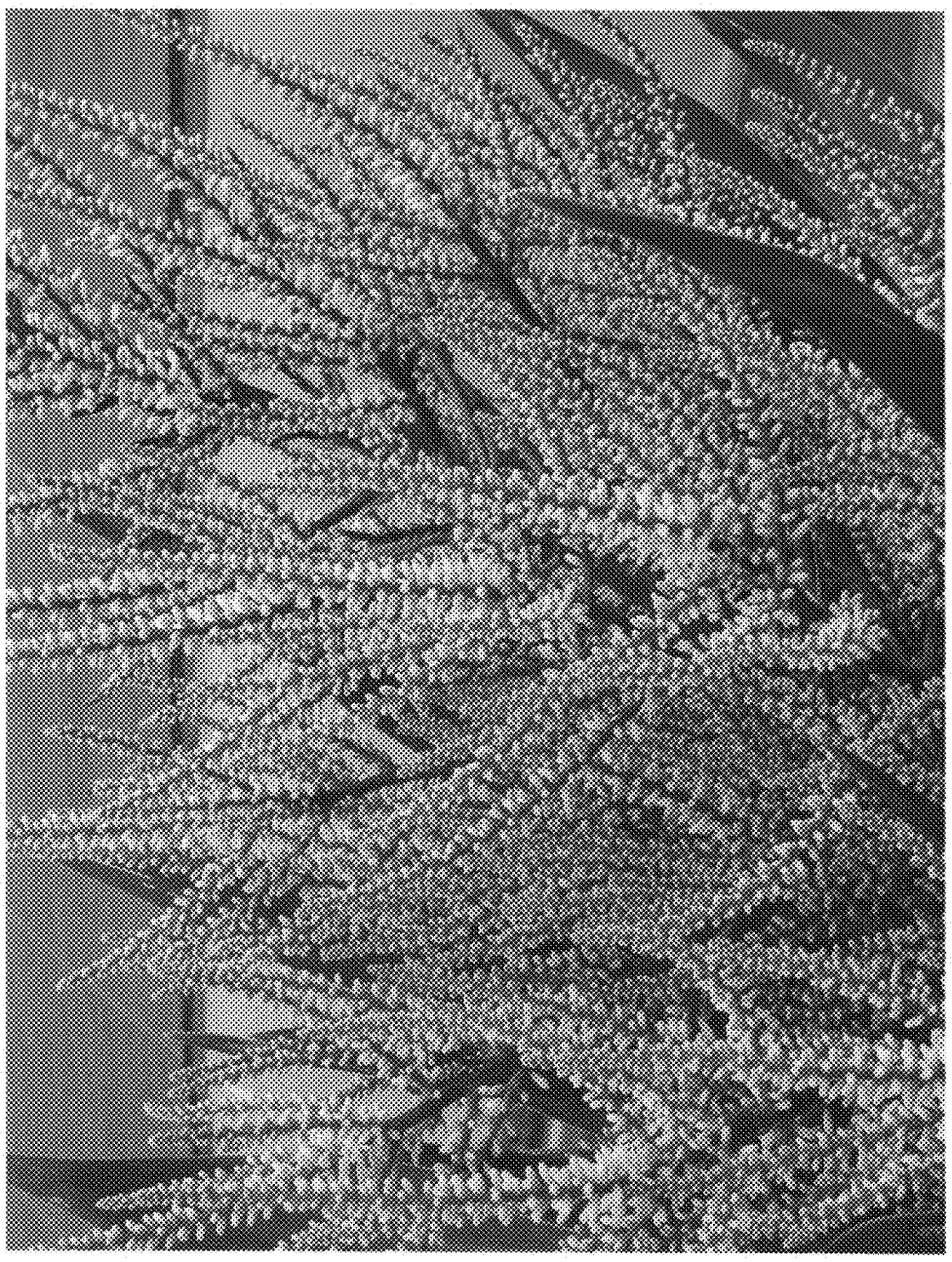

* * * * *